(12) United States Patent
Cho et al.

(10) Patent No.: US 6,221,639 B1
(45) Date of Patent: Apr. 24, 2001

(54) PROCESS FOR PREPARING OPTICALLY PURE(S)-3,4-DIHYDROXYBUTYRIC ACID DERIVATIVES

(75) Inventors: Yik-haeng Cho; Jongpil Chun; Young Mi Park; Kyoung Rok Roh; Hosung Yu; Dae Il Hwang, all of Daejeon (KR)

(73) Assignee: Samsung Fine Chemicals Co., Ltd., Ulsan (KR)

( * ) Notice: Subject to any disclaimer, the term of this patent is extended or adjusted under 35 U.S.C. 154(b) by 0 days.

(21) Appl. No.: 09/359,679

(22) Filed: Jul. 23, 1999

(30) Foreign Application Priority Data

Jul. 24, 1998 (KR) .................................................. 98-29912

(51) Int. Cl.$^7$ ....................................................... C12P 7/62
(52) U.S. Cl. ............................ 435/135; 435/96; 435/98; 435/146
(58) Field of Search ............................... 435/135, 96, 98, 435/146

(56) References Cited

U.S. PATENT DOCUMENTS

| | | |
|---|---|---|
| 3,791,865 | 2/1974 | Hurst et al. . |
| 3,922,200 | 11/1975 | Guillaume et al. . |
| 3,986,890 | 10/1976 | Richter et al. . |
| 4,138,484 | 2/1979 | Fuxe . |
| 4,447,532 | 5/1984 | Coker et al. . |
| 4,612,284 | 9/1986 | Pickens et al. . |
| 4,855,232 | 8/1989 | Takasaki . |
| 5,292,939 | 3/1994 | Hollingsworth . |
| 5,319,110 | 6/1994 | Hollingsworth . |
| 5,374,773 | 12/1994 | Hollingsworth . |
| 5,506,353 | 4/1996 | Subramaniam . |
| 5,808,107 | 9/1998 | Hollingsworth . |
| 5,998,633 | * 12/1999 | Jacks et al. ............................ 549/313 |

FOREIGN PATENT DOCUMENTS

| | | |
|---|---|---|
| 451142 A1 | 10/1991 | (EP) . |
| 64-13069 | 1/1989 | (JP) . |
| 4-148795 | 5/1992 | (JP) . |
| 4-149151 | 5/1992 | (JP) . |
| 6-172256 | 6/1994 | (JP) . |
| WO 93/06826 | 4/1993 | (WO) . |
| WO 94/05639 | 3/1994 | (WO) . |
| WO 98/04543 | 2/1998 | (WO) . |
| WO99/05092 | 4/1999 | (WO) . |

OTHER PUBLICATIONS

J. Am. Chem. Soc., 105, 5925–5926 (1983).
J. Am. Chem. Soc., 117, 1181 (1995).
J. Am. Chem. Society, 2245–2247 (1953).
J. Chem. Soc., 1924–1931 (1960).
J. Chem. Soc., 1932–1938 (1960).
J. Am. Chem. Soc., 1431–1435 (1955).
J. Am. Chem. Soc., 81, 3136 (1959).
Bull. Chem. Soc. Jpn., 61, 2025 (1988.
J. Org. Chem., 50, 1144 (1985).
Tetrahedron Letter, 46, 4277 (1990).
Tetrahedron Letter, 33, 2279 (1992).
Tetrahedron Lett., 507 (1992).
Tetrahedron Lett., 31, 267–270 (1990).
Chem. Lett., 1389–1392 (1984).
J. Res. Natl. Bur. Standards., vol. 32, No. 2, p. 45 (1944).
Can. J. Chem., 65, 195 (1987).
Carbohyd. Res., 11, 17–25 (1969).
Starch 41 Nr. 8, S. 303–309 (1989).
Synthesis, 597–613 (1997).
J. Chromatography, 549, 113–125 (1991).
Encyclopedia of Chemical Technology 3th ed. 491–507.
Methods Carbohydr. Chem., 10, 231–239 (1994).
Methods Carbohydr. Chem., 10, 245–248 (1994).

* cited by examiner

*Primary Examiner*—Herbert J. Lilling
(74) *Attorney, Agent, or Firm*—Finnegan. Henderson, Farabow, Garrett & Dunner, L.L.P.

(57) ABSTRACT

The present invention relates to a process for preparing optically pure (S)-3,4-dihydroxybutyric acid derivatives expressed by the following Formula 1 and more particularly, to a process that enables preparing optically pure (S)-3,4-dihydroxybutyric acid derivatives economically in large quantities, by:

(a) Preparing α-(1,4)-linked oligosaccharide with adequate sugar distribution by reacting amylopectin which is easily available from natural product with enzyme under a specific condition; and (b) Performing oxidation and esterification sequentially under a specific condition.

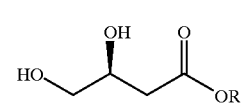

(1)

wherein, R represents linear or branched alkyl group with 1~5 carbon atoms.

14 Claims, 3 Drawing Sheets

PROCESS FOR PREPARING OPTICALLY PURE(S)-3,4-DIHYDROXYBUTYRIC ACID DERIVATIVES

BACKGROUND OF THE INVENTION

1. Field of the Invention

The present invention relates to a process for preparing optically pure (S)-3,4-dihydroxybutyric acid derivatives expressed by the following Formula 1 and more particularly, to a process that enables preparing optically pure (S)-3,4-dihydroxybutyric acid derivatives economically in large quantities, by:

(a) Preparing α-(1,4)-linked oligosaccharide with adequate sugar distribution by reacting amylopectin which is easily available from natural product with enzyme under a specific condition; and (b) Performing oxidation and esterification sequentially under a specific condition.

(1)

Wherein, R represents linear or branched alkyl group with 1~5 carbon atoms.

2. Description of the Related Arts (S)-3,4-Dihydroxybutyric acid derivatives and (S)-3-hydroxy-γ-butyrolactone are used as synthetic intermediates for preparing various chiral compounds. For example, it is well known that they act as key intermediates for preparing neuromeidator (R)-GABOB [*Tetrahedron*, 46, 4277(1990)], treatment for hyperlipemia (Atorvastatin; HMG—CoA reductase inhibitor) [*Tetrahedron Lett.*, 33, 2279(1992)], (S)-oxiracetam which is improvement agent in brain metabolism [International patent publication WO93/06,826], L-carnitine which is health supplement agent [International patent publication WO99/05,092], (S)-3-hydroxytetrahydrofuran [*J. Am. Chem. Soc.*, 117, 1181 (1995); International patent publication WO94/05,639] which is an essential intermediate of AIDS drug (Agenerase; HIV protease inhibitor), (S)-mono-betalactam [Japanese patent publication 64-13,069(1989)], ester of (S)-3-hydroxy-4-bromobutyric acid [Japanese patent publication 4-149,151(1992); Japanese patent publication 6-172,256 (1994)], potentiating intermediate of satiety agent [*Bull. Chem. Soc. Jpn.*, 61, 2025(1988)] and neuroleptic drug [U.S. Pat. No. 4,138,484] and useful intermediates in synthetic efforts towards natural products [*J. Org. Chem.*, 50, 1144 (1985); *Can. J Chem.*, 65, 195 (1987), *Tetrahedron Lett.*, 507 (1992)]. Optical purity is the most important factor in preparing these chiral compounds.

The conventional technologies for preparing (S)-3,4-dihydroxybutyric acid derivatives and (S)-3-hydroxy-γ-butyrolactone, which are useful for preparing the said chiral compounds, are explained in detail hereunder.

Methods of preparing (S)-3-hydroxybutyric acid derivatives from the enzymatic or catalytic reduction of β-ketoester were known [*J. Am. Chem. Soc.*, 105, 5925~5926(1983); *Teterahedron Lett.*, 31, 267~270(1990); European patent publication 452,143A2]. These methods have difficulty in that the prochiral center should be reduced to one-side to generate chiral center and expensive metal catalyst should be used.

A technology preparing ester of (S)-3,4-dihydroxybutyric acid and (S)-3-hydroxy-γ-butyrolactone by selective reduction of (L)-malic acid ester was known [*Chem. Lett.*, 1389~1392(1984); U.S. Pat. No. 5,808,107]. This technology has disadvantage in that reduction should be performed selectively to only one of the two ester functional groups.

Many methods of preparing (S)-3,4-dihydroxybutyric acid derivatives and (S)-3-hydroxy-γ-butyrolactone from carbohydrate have been reported.

A technology preparing isosaccharinic acid (B) or (S)-3,4-dihydroxybutyric acid (C) is reported [J. Chem. Soc., 1924~1931(1960)] by alkaline degradation of carbohydrate containing glucose substituent in the 4-position, such as 4-O-methyl-(D)-glucose, maltose, amylose and cellulose, elimination of C-4 substituent as leaving group, forming dicarbonyl compound (A; 4-deoxy-2,3-hexodiulose), and reacting the formed dicarbonyl compound with base as shown in Scheme 1. However, the yield of (S)-3,4-dihydroxybutyric acid is low.

Scheme 1

R = 1, 4-linked glucosan

Also, it has been reported that (S)-3,4-dihydroxybutyric acid (C) and glycolic acid (D) were obtained as major products by forming dicarbonyl compound (A) from alkaline degradation of carbohydrate containing glucose substituent in the 4-position, and separating the formed dicarbonyl compound (A) and reacting it with hydrogen peroxide [*J Chem. Soc.*, 1932~1938(1960)]. This method has a serious problem that the product exists as small amount of isomers due to tautomerization and a mixture of cyclic compounds and hydrates derived from dicarbonyl compound (A). So, the dicarbonyl compound (A) cannot be separated in good yields from the reaction mixture. Another problem is that the prepared (S)-3,4-dihydroxybutyric acid is degraded to formic acid and glycolic acid due to the overoxidation.

A similar technology for preparing (S)-3,4-dihydroxybutyric acid from carbohydrate either using base only or using oxygen in base was known. It proposed that the dicarbonyl compound (A) was a synthetic intermediate for (S)-3,4-dihydroxybutyric acid as shown in the Scheme 1. But the yield was reported to be as low as about 30% [*J. Res. Natl. Bur. Stand.*, 32, 45(1944); *J. Am. Chem. Soc.*, 2245~2247(1953); *J. Am. Chem. Soc.*, 1431~1435(1955); *Carbohyd. Res.*, 11, 17~25(1969); *J. Chromatography*, 549, 113~125(1991)]. In these methods, (S)-3,4-dihydroxybutyric acid is produced with various kinds of mixtures including glycolic acid (D), isosaccharinic acid (B), formic acid, ketone, diketone and glyceric acid. Since the yield of (S)-3,4-hydroxybutyric acid is very low, these methods are also considered as not suitable for industrial use.

A method for preparing (S)-3,4-dihydroxybutyric acid from disaccharide lactose) using base and oxidant has been reported [International patent publication WO98/04543]. In this work, (S)-3,4-dihydroxybutyric acid was cyclized to (S)-3-hydroxy-γ-butyrolactone under the reaction condition and purified by protection of the two hydroxy groups to acetonide ester compound, methyl (S)-3,4-O-isopropylidene-3,4-dihydroxybutanoate, which was recyclized to (S)-3-hydroxy-γ-butyrolactone under acidic media.

Preparing methods of (S)-3,4-dihydroxybutyric acid including the process of alkaline oxidation of carbohydrate containing glucose substituent in the 4-position have been known [U.S. Pat. Nos. 5,292,939, 5,319,110 & 5,374,773 (1994)]. In these methods, dicarbonyl compound (A) intermediate is formed at first, oxidized to (S)-3,4-dihydroxybutyric acid (C) and glycolyic acid (D). However, optical purity, the most important physical property of chiral compounds, is not mentioned at all. Also, purification of target compound is very difficult, considering the reaction mechanism. In the case of disaccharides such as maltose or lactose, only one sugar unit in the disaccharide forms (S)-3,4-dihydroxybutyric acid and the other sugar unit functions as leaving group, so that the target product and leaving group coexist as 1:1 mixture. Accordingly, it is very difficult to separate and purify (S)-3,4-dihydroxybutyric acid or (S)-3-hydroxy-γ-butyrolactone from the reaction mixture. The theoretical mass conversion obtainable is 28.3 wt %. In other words, 28.3 g of (S)-3-hydroxy-γ-butyrolactone can be obtained from 100 g of disaccaride. For polysaccharides, such as maltodextrin, starch and cellulose, mentioned in the above patents, the (1,4) and/or (1,6) glucose units are linked complexly like nets. The problem is that the step-by-step oxidation proceeding from the reducing end units comprising (1,4) linkage terminates at (1,6) linkage unit. Therefore, no more target product is formed. Also, the polysaccharides are degraded by overoxidation of reducing end units to complex acid mixtures containing formic acid, oxalic acid, glycolic acid and erythronic acid [*J. Am. Chem. Soc.*, 81, 3136(1959); *Starch* 41 Nr. 8, S. 303~309(1989); *Synthesis*, 597~613(1997)].

There was an attempt to improve the yield of (S)-3,4-dihydroxybutyric acid or (S)-3-hydroxy-γ-butyrolactone for polysaccharide by degradation of higher-molecular sugars to relatively lower-molecular sugars through acid or base hydrolysis. Though the reactivity by this method is increased to a degree, (1,4) linkage and (1,6) linkage are not hydrolyzed selectively to afford random distribution. Accordingly, there is a fundamental problem in preparing (S)-3,4-dihydroxybutyric acid derivatives in high yield [*Encyclopedia of Chemical Technology*, 3rd ed. 492~507].

Regarding the preparation of (S)-3-hydroxy-γ-butyrolactone using (1,4) linked polysaccharide, the step-by-step oxidation proceeds continuously from the reducing end units to non-reducing end units to afford (S)-3,4-dihydroxybutyric acid until the last chain unit (a leaving group) remained. Namely, if (1,4)-linked polysaccharide is used as a source material for preparing (S)-3-hydroxy-γ-butyrolactone, the theoretical mass conversion obtainable is 63 wt %, about two times more compared with the method using disaccharide. In other words, 63 g of (S)-3-hydroxy-γ-butyrolactone can be obtained from 100 g of (1,4)-linked polysaccharide. Also, since the small amount of leaving group is produced in the reaction mixture compared with disaccharide, the target product is easily purified. Therefore, the use of (1,4)-linked polysaccharide promises the enhanced productivity.

However, regarding conventional polysaccharides, the target product and by-products (acids such as formic acid, oxalic acid, glycolic acid and erythronic acid) are formed competitively in the step-by-step oxidation due to the compact structure having random (1,4) linkage and (1,6) linkage. Thus, selective degradation technique of polysaccharide to a suitable sugar distribution range having (1,4) linkage is required.

On the other hand, there have been many reports of transforming higher-molecular sugars to lower-molecular sugars using biological enzymatic treatment process for industrial use.

The reported technologies include preparing glucose, maltose and ethanol through enzymatic treatment of starch [U.S. Pat. No. 3,791,865(1974); U.S. Pat. No. 3,922,200

(1975); U.S. Pat. No. 4,855,232(1989): Japanese patent publication 4-158,795(1992); *Methods Carbohydr. Chem.*, 10, 231~239(1994); *Methods Carbohydr. Chem.*, 10, 245~248(1994)], and preparing maltodextrin with adequate dextrose equivalent (DE) [U.S. Pat. No. 3,986,890(1976); U.S. Pat. No. 4,447,532(1984); U.S. Pat. No. 4,612,284 (1986); U.S. Pat. No. 5,506,353(1996)]. In these references, through the degradation or transformation of high molecular polysaccharides, they are converted to adequate materials for medicines, food additives and diagnostic reagents.

But, the method for preparing α-(1,4) linked oligosaccharides with suitable sugar distribution for the production of (S)-3,4-dihydroxybutyric acid derivatives is not known at present.

SUMMARY OF THE INVENTION

The inventors of the present invention made intensive efforts to develop a method for preparing optically pure (S)-3,4-dihydroxybutyric acid derivatives from commercially available amylopectin with ease. As a result, a process which enables preparing optically pure (S)-3,4-dihydroxybutyric acid derivatives economically in large quantities is found by preparing oligosaccharide with structural specificity which can minimize formation of by-products from amylopectin by enzymatic reaction. Furthermore, oxidation reaction can be performed continuously in the same reactor without additional separation and purification of the above prepared oligosaccharide.

Accordingly, an object of this invention is to provide a method for preparing optically pure (S)-3,4-dihydroxybutyric acid derivatives in high yield without additional purification of intermediates.

DETAILED DESCRIPTION OF THE INVENTION

The present invention is characterized by comprising the following steps:

(a) Enzymatic reaction of amylopectin to α-(1,4) linked oligosaccharide expressed by the Formula 2; and (b) Oxidation of the oligosaccharide with oxidant in base, and subsequent esterification with alcohol in the presence of an acid catalyst to afford ester of (S)-3,4-dihydroxybutyric acid derivatives expressed by the Formula 1.

, wherein R represents linear or branched alkyl group with 1~5 carbons.

The detailed description of the present invention is given hereunder.

The fundamental inventive concept of the present invention is selective degradation of α-(1,4) linkage and α-(1,6) linkage within amylopectin using specific enzymes, i.e., transforming amylopectin to α-(1,4)-inked oligosaccharide with the optimal sugar distribution for preparing the target compound. And subsequently oxidation and esterification are performed to prepare (S)-3,4-dihydroxybutyric acid derivatives.

Namely, focusing on the specificity of enzymes, amylopectin is degraded sequentially with specific enzymes to α-(1,4) linked oligosaccharide, and optically pure (S)-3,4-dihydroxybutyric acid derivatives are prepared from the transformed oligosaccharide in high yield. Optical purity of the desired product prepared by a sequential method is over 99.9% ee.

Oligosaccharide used in the present invention is prepared with biological enzymatic treatment of amylopectin, and amylopectin is commercially available with ease. Especially, since amylopectin is highly soluble in water or in buffer solution of pH 4.0~8.0, used as reaction solvent for enzymatic reaction of the present invention, the relative reactivity to enzyme is greatly increased compared with other polysaccharides such as starch and cellulose. Thus, the same is very effective material for preparing of oligosaccharide having suitable sugar distribution for the preparation of (S)-3,4-dihydroxybutyric acid derivatives.

When using pullulanase as an enzyme for selective degradation of α-(1,6) linkage in amylopectin, it causes the solubility problem of amylopectin and reduced enzyme activity. So, rather than using pullulanase only, α-amylase was used to improve reactivity in degrading amylopectin to a suitable sugar distribution, and then pullulanase was used. However, in this case, activity of the remaining α-amylase persists and thus amylopectin is degraded excessively, so that the desired oligosaccharide is not formed. Accordingly, a technology of inactivating the remaining α-amylase before the pullulanase reaction was introduced.

The detailed explanation of the preparation process of this invention is as follow. It comprises; 1) a step preparing oligosaccharide with characteristic α-(1,4) linkage expressed in Formula 2 by selective degradation of amylopectin using biological treatment of specific enzymes, and 2) a step preparing optically pure (S)-3,4-dihydroxybutyric acid derivatives by esterifying (S)-3,4-dihydroxybutyric acid salt formed through oxidation. Especially, the preparation process of this invention is characterized by preparing (S)-3,4-dihydroxybutyric acid derivatives in the same reactor without additional purification of the intermediates (oligosaccharide and (S)-3,4-dihydroxybutyric acid).

The enzymatic reaction of the present invention uses α-amylase and pullulanase sequentially. α-Amylase degrades α-(1,4) linkage and pullulanase degrades α-(1,6) linkage selectively.

The superiority of the present invention lies in that optically pure (S)-3,4-dihydroxybutyric acid derivatives are prepared in high yield under a mild reaction condition by using enzymes selectively degrading α-(1,4) linkage or α-(1,6) linkage, while the chemical hydrolysis method has no selectivity.

The enzymatic reaction of the present invention is performed in water or buffer solution of pH 4.0~8.0 at 40~120° C. α-Amylase is used in the range of 0.001~10 wt % of amylopectin, and enzymatic reaction of α-amylase is performed for 30 min~4 hr, and then remaining α-amylase is inactivated. Inactivation is performed under acidic (pH 2.0~4.5) and high temperature (60~150° C.) conditions and maintained for 10 min~4 hr. In the enzymatic reaction of pullulanase, pullulanase is used in the range of 0.001~10 wt % of amylopectin, and most of the oligosaccharides distribute within 3~50 glucose units by 10~40 hr of the pullulanase enzymatic treatment. Reducing end units and molecular weight distribution of the prepared oligosaccharide are analyzed from reducing end units and dextrose equivalent analysis by an optical analyzer, HPLC analysis, and gel permeation chromatography (GPC) analysis.

The oligosaccharide is obtained from the selective enzymatic reaction and has distribution mostly between 3~50 glucose units, and preferably 5~50 glucose units. Since most of the glucose units are linked with α-(1,4) linkage, (S)-3,4-dihydroxybutyric acid derivatives can be obtained in high yield through continuous sequential reactions with minimizing the by-products (e.g., acid mixtures of formic acid, oxalic acid, glycolic acid and erythronic acid). Furthermore, the obtained (S)-3,4-dihydroxybutyric acid derivatives were identified to be optically very pure (>99.9% ee).

Oxidation of oligosaccharide is performed by adding base and oxidant dropwise for 6~36 hr under the condition of 30~65° C. Hydrogen peroxide, alkali metal peroxides, akaline earth metal peroxides and alkyl hydroperoxides are used for the oxidants, and hydrogen peroxide is the most preferable. The oxidant is used in the range of 1~3 equivalents per molar glucose unit of amylopectin. The base is selected from the group consisting of alkali metal hydroxide or alkaline earth metal hydroxide, and sodium hydroxide or potassium hydroxide is preferable. The base is used in the range of 2~4 equivalents per molar glucose unit of amylopectin.

Esterification of the present invention is performed in the presence of acid catalyst using alcohol as both a reaction solvent and reagent in the range of 30~80° C. Inorganic acids such as hydrochloric acid, sulfuric acid, phosphoric acid and nitric acid, or organic acids such as fluoroalkylsulfonic acid, aralkylsulfonic acid, hydrate of aralkylsulfonic acid and trifluoroacetic acid are used as acid catalyst. Linear or branched alcohol with 1~5 carbon atoms is used for the alcohol.

In order to compare the preparation yields depending on the source material of oxidation, the prepared (S)-3,4-dihydroxybutyric acid derivatives were cyclized (S)-3-hydroxy-γ-butyrolactone as follows [Refer to Experimental example 1.]. (S)-3,4 -dihydroxybutyric acid derivatives were cyclized in the presence of acid catalyst by agitating the same for 2~5 hr in the range of 30~80° C. to obtain (S)-3-hydroxy-γ-butyrolactone. Inorganic acids such as hydrochloric acid, sulfuric acid, phosphoric acid and nitric acid, or organic acids such as fluoroalkylsulfonic acid, aralkylsulfonic acid, hydrate of aralkylsulfonic acid and trifluoroacetic acid are used as acid catalyst. As a result, if maltose (disaccharide) or lactose (disaccharide) obtained from cheese by-product is used as source material, the theoretical mass conversion yield of (S)-3-hydroxy-γ-butyrolactone is not more than 28.3 wt % of the source material weight used. On the other hand, if amylose (α-(1,4) linked polysaccharide) with more than 50 glucose units is used, the theoretical mass conversion yield of (S)-3-hydroxy-γ-butyrolactone is equal to that of amylopectin. But, the double helix structure due to very strong intramolecular hydrogen bond limits the step-by-step oxidation, so the yield becomes very low. However, by using oligosaccharide of the present invention is used as source material, the yield of (S)-3-hydroxy-γ-butyrolactone is very high as 57.2 wt % of the source material weight used.

As explained above, the present invention is excellent in that the low reactivity of amylopectin to oxidation is overcome by transforming amylopectin to oligosaccharide with the application of specific enzymes. Furthermore, by-product formation is minimized and optically pure (S)-3,4-dihydroxybutyric acid derivatives can be prepared in high yield with very simple purification process.

The following examples are intended to be illustrative of the present invention and should not be construed as limiting the scope of this invention defined by the appended claims.

EXAMPLE 1

Preparation of Methyl (S)-3,4-Dihydroxybutanoate

10 L of water and 5 kg of dried amylopectin were put into a 50 L reactor. After heating the reactor to 55° C., 12 g of α-amylase (BAN; EC 3.2.1.1 from *Bacillus licheniformis*, Novo Nordisk) was added. After heating this reaction solution to 75° C., the same was stirred for 2 hr at the same temperature. 5 mL of 0.1N HCl solution was added to adjust the pH 3.0~3.5, and then the same was stirred for 1 hr at 90° C. to inactivate the remaining α-amylase. After slowly cooling the reaction mixture to 30° C., 3.7 L of 4M acetic acid buffer solution (pH 5) and 1.3 L of water were added to adjust the pH to 5. The reaction solution was heated to 60° C., and then 62.5 g of pullulanase (Promozyme; EC 3.2.1.4 from *Bacillus acidopullulyticus*, Novo Nordisk) was added and the solution was stirred for 22 hr at the same temperature. 0.54 kg of 40% NaOH solution was added to the reaction solution to neutralize acetic acid and the temperature was raised to 60° C. 40% NaOH (8.64 kg) solution and 30% $H_2O_2$ (5.25 kg) solution were added dropwise for 24 hr to the reaction solution and the same was stirred for 1 hr at the same temperature. The prepared sodium salt of (S)-3,4-dihydroxybutyric acid was identified using NMR analysis.

$^1$H-NMR ($D_2O$, ppm) δ 2.27 (dd, 1H), 2.39 (dd, 1H), 3.41 (dd, 1H), 3.51 (dd, 1H), 3.8~3.9 (m, 1H)

The reaction solution was concentrated, and 10 L of methanol was added. Sulfuric acid were added to adjust the pH to 4~5, and then the same was stirred for 3 hr at 50° C. Sodium carbonate was added to neutralize the solution, and the same was filtered to remove the by-product, and then methanol was concentrated to obtain methyl (S)-3,4-dihydroxybutanoate. The formation of methyl (S)-3,4-dihydroxybutanoate (conversion ratio: 92%) was identified through NMR analysis by comparison with internal standard.

$^1$H-NMR ($CDCl_3$, ppm) δ 2.5 (dd, 2H), 3.5 (dd, 1H), 3.6 (dd, 1H), 3.7 (s, 3H), 4.1 (m, 1H)

EXAMPLE 2

Preparation of (S)-3-Hydroxy-γ-Butyrolactone

10 L of water and 5 kg of dried amylopectin were put into a 50 L reactor. After heating the reactor to 55° C., 12 g of α-amylase (Teramyl; EC 3.2.1.1 from *Bacillus amyloliquefaciens*, Novo Nordisk) was added. After heating this reaction solution to 85° C., the same was stirred for 2 hr at the same temperature. 5 mL of 0.1N HCl solution was added to adjust the pH 3.0~3.5, and then the same was stirred for 1 hr at 90° C. to inactivate the remaining α-amylase. After slowly cooling the reaction to 30° C., 3.7 L of 4M acetic acid buffer solution (pH 5) and 1.3 L of water were added to adjust the pH to 5. The reaction solution was heated to 60° C., and then 62.5 g of pullulanase (Promozyme; EC 3.2.1.4 from *Bacillus acidopullulyticus*, Novo Nordisk) was added and the solution was stirred for 22 hr at the same temperature. 0.54 kg of 40% NaOH solution was added to the reaction solution to neutralize acetic acid and the temperature was raised to 60° C. 40% NaOH (8.64 kg) solution and 30% $H_2O_2$ (5.25 kg) solution were added dropwise for 24 hr to the reaction solution and the same was stirred for 1 hr at the same temperature. The prepared sodium salt of (S)-3,4-dihydroxybutyric acid was identified using NMR analysis.

$^1$H-NMR ($D_2O$, ppm) δ 2.27 (dd, 1H), 2.39 (dd, 1H), 3.41 (dd, 1H), 3.51 (dd, 1H), 3.8~3.9 (m, 1H)

The reaction solution was concentrated, and 10 L of methanol was added. In this solution, methanesulfonic acid was added to adjust the pH to 4~5, and then the same was stirred for 3 hr at 50° C. After cooling, sodium carbonate was added to neutralize the solution, and the same was filtered to remove the by-product, and then methanol was concentrated to obtain methyl (S)-3,4-dihydroxybutanoate. Formation of methyl (S)-3,4-dihydroxybutanoate (conversion ratio: 93%) was identified using NMR analysis by comparison with the internal standard.

$^1$H-NMR ($CDCl_3$, ppm) δ 2.5 (dd, 2H), 3.5 (dd, 1H), 3.6 (dd, 1H), 3.7 (s, 3H), 4.1 (m, 1H)

The prepared methyl (S)-3,4-dihydroxybutanoate was cyclized at 65° C. under reduced pressure by adding 0.5 wt % of concentrated HCl without any separation being performed. The resultant solution was dissolved with ethyl acetate and the same was neutralized with sodium carbonate. After filtrating and concentrating the same, (S)-3-hydroxy-γ-butyrolactone (2.86 kg, 57.2 wt % of the amylopectin weight used) was obtained.

$^1$H-NMR ($CDCl_3$, ppm) δ 2.28 (dd, 1H), 2.74 (dd, 1H), 4.13 (dd, 1H), 4.32 (dd, 1H), 4.4~4.5 (m, 1H)

EXAMPLE 3

Preparation of (S)-3-Hydroxy-γ-Butyrolactone

As in the Example 2, however using 1 wt % of methanesulfonic acid rather than concentrated HCl in the cyclization of the prepared methy (S)-3,4-dihydroxybutanoate, the same was cyclized at 65° C. under reduced pressure. The resultant solution was dissolved with ethyl acetate and the same was neutralized with sodium carbonate. After filtering and concentrating the same, (S)-3-hydroxy-γ-butyrolactone (2.85 kg, 57 wt % of the amylopectin weight used) was obtained.

$^1$H-NMR ($CDCl_3$, ppm) δ 2.28 (dd, 1H), 2.74 (dd, 1H), 4.13 (dd, 1H), 4.32 (dd, 1H), 4.4~4.5 (m, 1H)

EXAMPLE 4

Preparation of Methyl (S)-3,4-Dihydroxybutanoate

As in the Example 1, however using t-butylhydroperoxide (4.16 kg) rather than $H_2O_2$ for the oxidant, methyl (S)-3,4-dihydroxybutanoate was obtained. The formation of methyl (S)-3,4-dihydroxybutanoate (conversion ratio: 91%) was identified using NMR analysis by comparison with internal standard.

$^1$H-NMR ($CDCl_3$, ppm) δ 2.5 (dd, 2H), 3.5 (dd, 1H), 3.6 (dd, 1H), 3.7 (s, 3H), 4.1 (m, 1H)

COMPARATIVE EXAMPLE 1

Preparation of (S)-3-Hydroxy-γ-Butyrolactone from Starch

20 L of water and 5 kg of dried starch were put into a 50 L reactor, and the temperature was raised to 70° C. 40% NaOH (8.64 kg) solution and 30% $H_2O_2$ (5.25 kg) solution were added dropwise for 48 hr to the reaction solution and the same was stirred for 1 hr at the same temperature. The same was esterified and cyclized as in Example 2 to obtain (S)-3-hydroxy-γ-butyrolactone (1.1 kg, 22.0 wt % of starch weight used).

COMPARATIVE EXAMPLE 2

Preparation of (S)-3-Hydroxy-γ-Butyrolactone from Starch

10 L of 0.5N HCl solution and 5 kg of dried starch were put into a 50 L reactor, and the starch was hydrolyzed for 20 min at 100° C. After cooling the solution to 20° C., the same was neutralized with 100 mL of 40% NaOH solution and the temperature was raised to 70° C. 40% NaOH (8.64 kg) solution and 30% $H_2O_2$ (5.25 kg) solution were added dropwise for 48 hr to the reaction solution and the same was stirred for 1 hr at the same temperature. The same was esterified and cyclized as in Example 2 to obtain (S)-3-hydroxy-γ-butyrolactone (1.22 kg, 24.4 wt % of starch weight used).

COMPARATIVE EXAMPLE 3

Preparation of (S)-3-Hydroxy-γ-Butyrolactone from Amylose

20 L of water and 5 kg of dried amylose were put into a 50 L reactor, and the temperature was raised to 70° C. 40% NaOH (8.64 kg) solution and 30% $H_2O_2$ (5.25 kg) solution were added dropwise for 48 hr to the reaction solution and the same was stirred for 1 hr at the same temperature. The same was esterified and cyclized as in the Example 2 to obtain (S)-3-hydroxy-γ-butyrolactone (1.35 kg, 27.0 wt % of amylose weight used).

EXPERIMENTAL EXAMPLE 1

Comparison of (S)-3-Hydroxy-γ-Butyrolactone Yield Depending on the Source Material For the reaction solutions containing each of the carbohydrates shown in Table 1, oxidation, esterification and cyclization were performed as in the Example 2 to obtain (S)-3,4-dihydroxybutyric acid derivatives, and subsequently cyclized to obtain (S)-3-hydroxy-γ-butyrolactone. The yields of (S)-3-hydroxy-γ-butyrolactone are shown in Table 1.

TABLE 1

| Source material (5 kg) | Product (wt % compared with source material weight) |
| --- | --- |
| Oligosaccharide of the present invention (Example 2) | 2.86 kg (57.2 wt %) |
| Polysaccharide Amylopectin | 1.01 kg (20.2 wt %) |
| Amylose | 1.35 kg (27.0 wt %) |
| Disaccharide (maltose)[a)] | 1.19 kg (23.7 wt %) |

[a)]Examples 1 & 2 of USP 5,292,939, 5,319,110 & 5,374,773

Table 1 shows that for disaccharide the relative mass conversion yield is low as 23.7 wt %. On the other hand, if amylopectin is transformed to oligosaccharide with specific enzyme treatment, the relative mass conversion yield is enhanced to 57.2 wt %, almost two times compared with disaccharide. If amylopectin is not treated with enzymes, the relative mass conversion yield is relatively low as 20.2 wt %.

EXPERIMENTAL EXAMPLE 2

Optical Purity Analysis of (S)-3-Hydroxy-γ-Butyrolactone (S)-3-Acetoxy-γ-butyrolactone was synthesized by the following method in order to analyze optical purity of (S)-3-hydroxy-γ-butyrolactone prepared from the present invention and the conventional preparing method.

102 mg (1 mmol) of (S)-3-hydroxy-γ-butyrolactone prepared from each method was dissolved in 3 mL of methylene chloride, and 0.4 mL (5 mmol) of pyridine and 0.47 mL (5 mmol) of acetic anhydride were added to the same. After 3 hr, the reaction was quenched with 1N HCl (S)-3-Acetoxy-γ-butyrolactone was extracted with the methylene chloride. After work up, the same was purified with silica gel column chromatography. The obtained (S)-3-acetoxy-γ-butyrolactone was dissolved in methylene chloride, and 0.5° C. was taken with syringe for GC analysis. The result is shown in the following Table 2 and FIGS. 1a~1c.

TABLE 2

| Source Material | Optical Purity |
| --- | --- |
| Disaccharide (maltose)[a)] | 94% ee |
| Oligosaccharide of the present invention (Example 2) | 99.9% ee |

[a)]Examples 1 & 2 of USP 5,292,939, 5,319,110 & 5,374,773

Figure 1A:
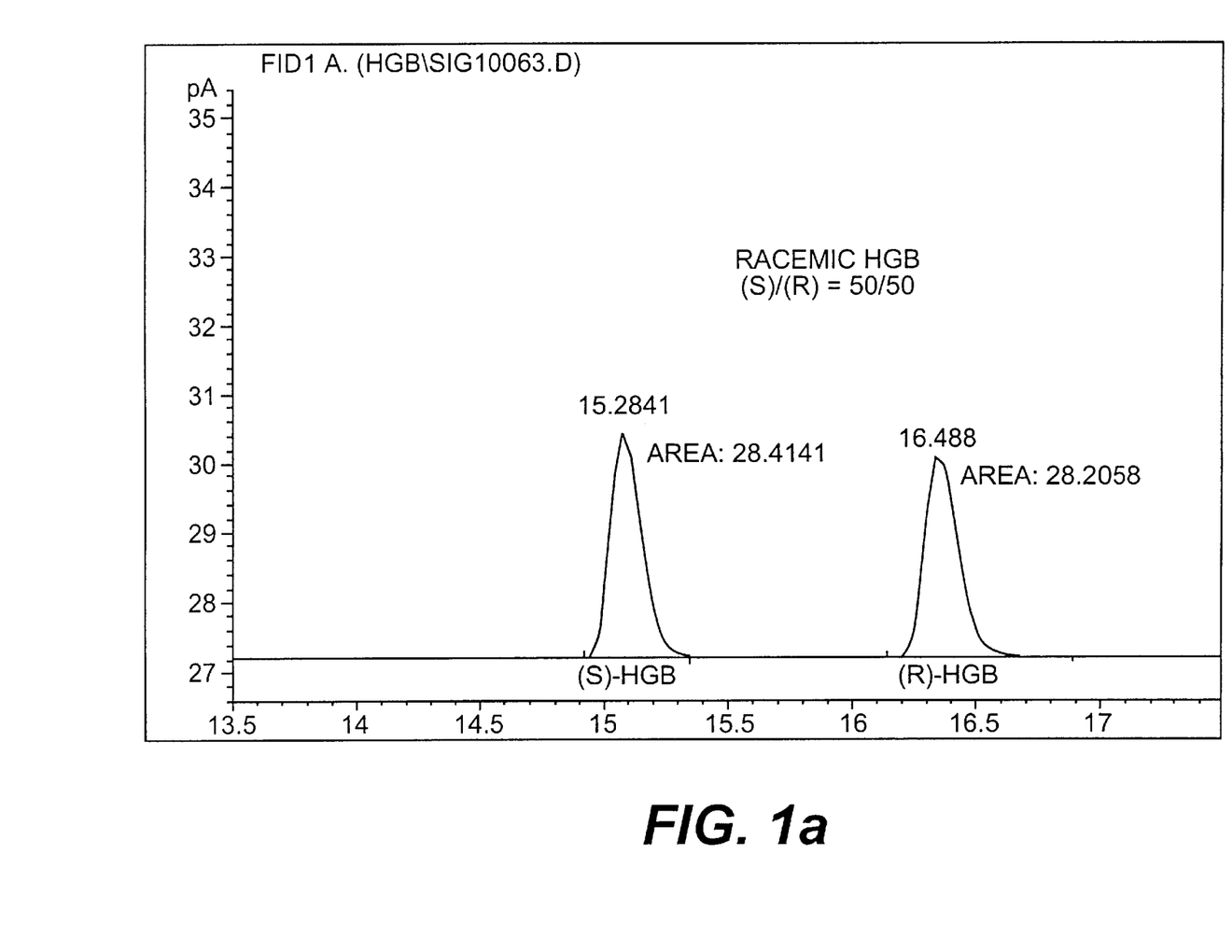
FIG. 1a represents the optical purity analysis results by gas chromatography (GC) of racemic 3-hydroxy-γ-butyrolactone.
Figure 1B:
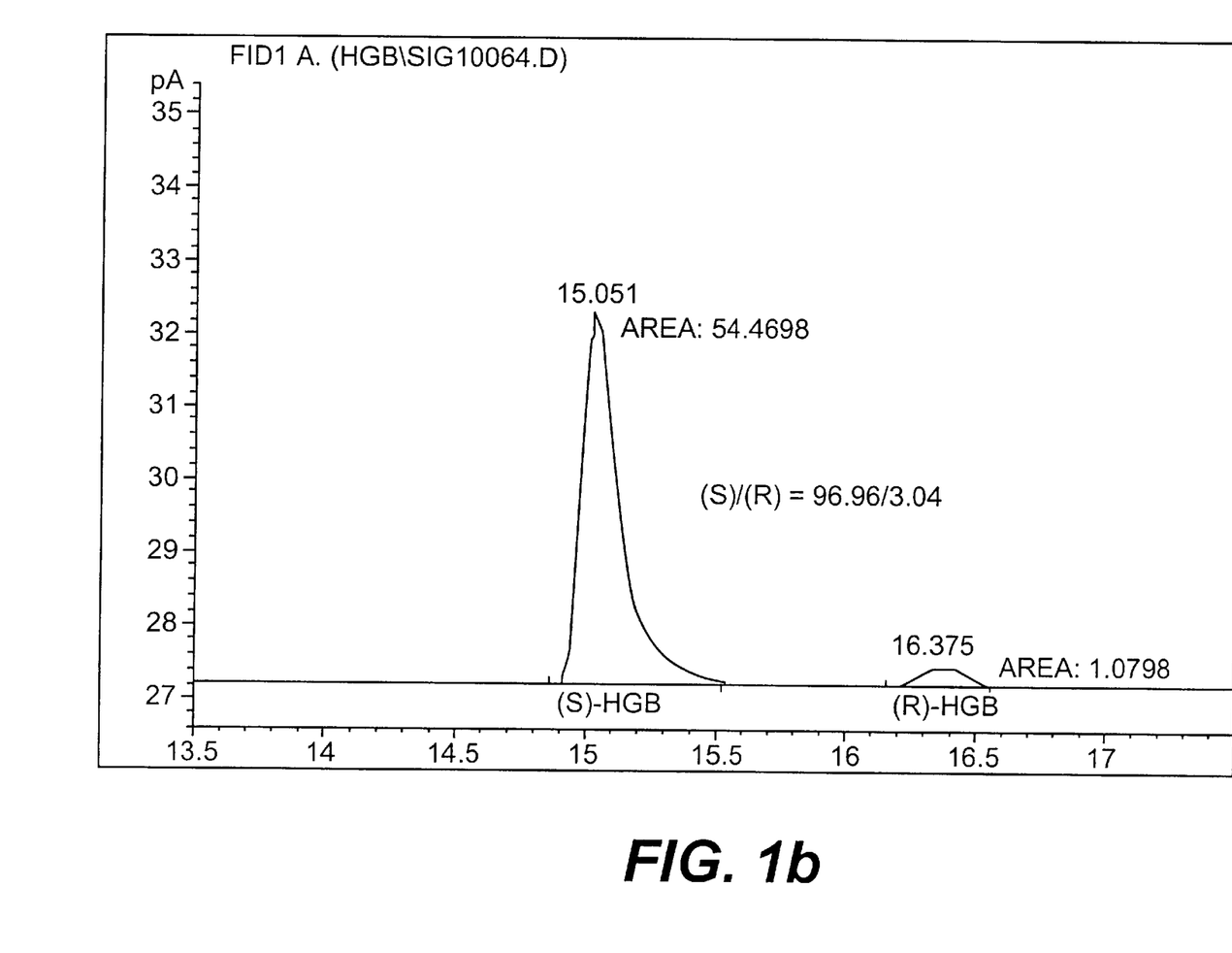
FIG. 1b represents the optical purity analysis results by gas chromatography (GC) of 3-hydroxy-γ-butyrolactone prepared from disaccharide of the conventional method.
Figure 1C:
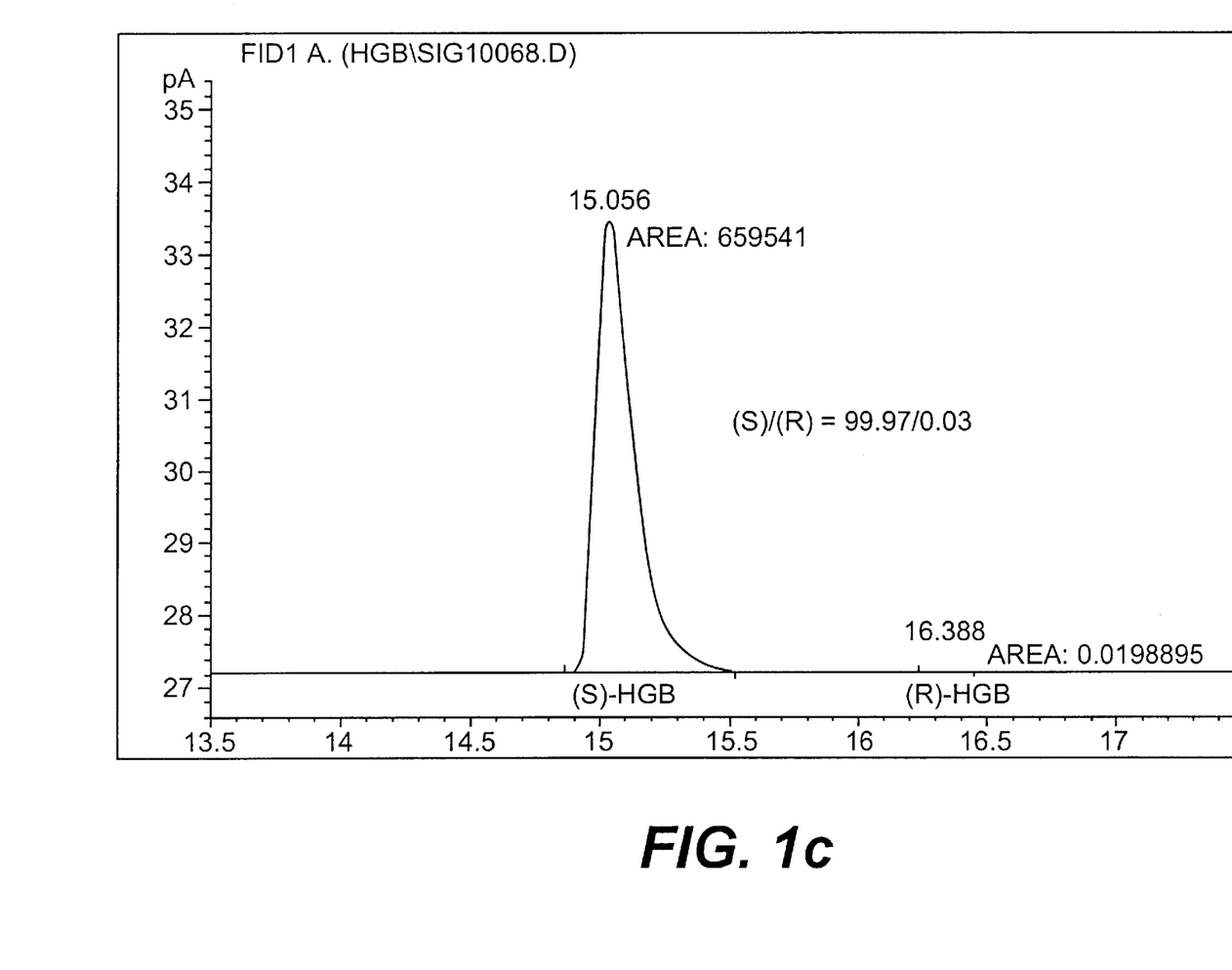
FIG. 1c represents the optical purity analysis results by gas chromatography (GC) of 3-hydroxy-γ-butyrolactone prepared from oligosaccharide of the present invention.

To improve the medicinal efficiency and minimize the side effect, more than 99.5% ee of high optical purity is required for chiral compounds. Table 2 and FIGS. 1a~1c show that the optical purity of (S)-3-hydroxy-γ-butyrolactone prepared from the present invention is very high as 99.9% ee. So, the same is very useful for the intermediates of other chiral compounds. The results are illustrated in FIGS. 1a, 1b, and 1c, respectively

The preparing method of the present invention gives optically pure (S)-3,4-dihydroxybutyric acid derivatives, which is very useful for industrial uses because the by-product formation is minimized and the purification process is very simple. It comprises alkaline oxidation of α-(1,4)-linked oligosaccharide from the enzymatic reaction of amylopectin in a specific condition followed by esterifying to afford the target product. The present invention has overcome the disadvantage of using expensive metal catalyst for selective asymmetric reduction, and enables easy preparation from inexpensive natural product having optically pure chiral center, thereby the industrial utility as chiral intermediates of various medicine can be maximized. Furthermore, the relative mass conversion yield is almost double compared with disaccharides.

What is claimed is:

1. A process for producing optically pure (S)-3,4-dihydroxybutyric acid derivatives expressed by the following Formula 1 from polysaccharide source comprising:

enzymatic reaction of amylopectin to α-(1,4) linked oligosaccharide expressed by the Formula 2, said enzymatic reaction comprising selective degradation of α-(1,4) and α-(1,6) linkages; and oxidation of the oligosaccharide with oxidant in base, and subsequent esterification with alcohol in the presence of an acid catalyst, wherein R represents linear or branched alkyl group with 1~5 carbon atoms.

2. The process according to claim 1, wherein the said oligosaccharide has 3~50 glucose units.

3. The process according to claim 1, wherein the said oxidation is performed in the temperature range of 30~65° C.

4. The process according to claim 1, wherein the base used in the said oxidation is selected from alkali metal hydroxide and alkaline earth metal hydroxide.

5. The process according to claim 4, wherein the said base is sodium hydroxide.

6. The process according to claim 1 or claim 4, wherein the said base is used in the range of 2~4 equivalents per molar glucose unit of amylopectin.

7. The process according to claim 1, wherein the oxidant used in the said oxidation is selected from hydrogen peroxide, alkali metal peroxide, alkaline earth metal peroxide and alkyl hydroperoxide.

8. The process according to claim 7, wherein the said oxidant is hydrogen peroxide.

9. The process according to claim 7, wherein the said oxidant is t-butylhydroperoxide.

10. The process according to claim 1 or claim 7, wherein the said oxidant is used in the range of 1~3 equivalents per molar glucose unit of amylopectin.

11. The process according to claim 1, wherein the said esterification is performed in the temperature range of 30~80° C.

12. The process according to claim 1, wherein the acid catalyst used in the said esterification is an inorganic acid selected from hydrochloric acid, sulfuric acid, phosphoric acid and nitric acid.

13. The process according to claim 1, wherein the acid catalyst used in the said esterification is an organic acid selected from fluoroalkylsulfonic acid, aralkylsulfonic acid, hydrate of aralkylsulfonic acid and trifluoroacetic acid.

14. The process according to claim 1, wherein α-amylase degrades the α-(1,4) linkage and pullulanase degrades the α-(1,6) linkage.

* * * * *

UNITED STATES PATENT AND TRADEMARK OFFICE
CERTIFICATE OF CORRECTION

PATENT NO. : 6,221,639 B1
DATED : April 24, 2001
INVENTOR(S) : Yik-haeng Cho et al.

It is certified that error appears in the above-identified patent and that said Letters Patent is hereby corrected as shown below:

<u>Title page, Item 54, column 1,</u>
PURE(S)-3,4-DIHYDROXYBUTYRIC" should read -- PURE(S) -3, 4-DIHYDROXYBUTYRIC --.

Signed and Sealed this

Eighteenth Day of September, 2001

Attest:

*Nicholas P. Godici*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

PATENT NO. : 6,221,639 B1
DATED : April 24, 2001
INVENTOR(S) : Yuk-haeng Cho et al.

It is certified that error appears in the above-identified patent and that said Letters Patent is hereby corrected as shown below:

Title page,
Item [54], PURE(S)-3,4-DIHYDROXYBUTYRIC" should read -- PURE (S)-3,4-DIHYDROXYBUTRIC --.

This Certificate supersedes Certificate of Correction issued September 18, 2001

Signed and Sealed this

Twenty-fifth Day of December, 2001

Attest:

Attesting Officer

JAMES E. ROGAN
Director of the United States Patent and Trademark Office